United States Patent [19]
Reisdorff et al.

[11] 3,966,725
[45] June 29, 1976

[54] 1-(4-PHENOXY-PHENYL)-1,3,5-TRIAZINES

[75] Inventors: Josef Helmut Reisdorff; Gerd Aichinger; Axel Haberkorn, all of Wuppertal-Elberfeld; Heinrich Kölling, Haan; Eckart Kranz, Wuppertal-Elberfeld, all of Germany

[73] Assignee: Bayer Aktiengesellschaft, Germany

[22] Filed: Mar. 18, 1975

[21] Appl. No.: 559,562

[30] Foreign Application Priority Data
Mar. 21, 1974 Germany............................ 2413722

[52] U.S. Cl............................ 260/248 NS; 424/249
[51] Int. Cl.²..................................... C07D 251/34
[58] Field of Search............................ 260/248 NS

[56] References Cited
FOREIGN PATENTS OR APPLICATIONS

| 250,977 | 12/1966 | Austria |
| 2,049,002 | 3/1971 | France |
| 2,038,685 | 4/1971 | Germany |
| 2,033,687 | 1/1972 | Germany |
| 1,770,991 | 2/1972 | Germany |
| 488,727 | 5/1970 | Switzerland |

*Primary Examiner*—John M. Ford

[57] ABSTRACT

1-(4-Phenoxy-phenyl)-1,3,5-triazine derivatives of the formula

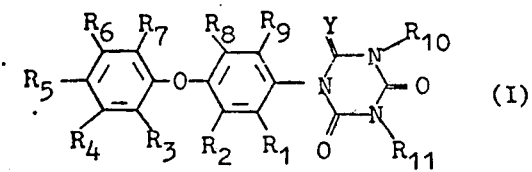

and pharmaceutically-acceptable, nontoxic salts thereof wherein $R_1$ to $R_9$ are the same or different and each is hydrogen, alkyl, haloalkyl, alkoxy, haloalkoxy, alkylthio, haloalkylthio, halo, nitro, cyano, amino, acylamino, alkoxycarbonylamino, carboxy, alkoxycarbonyl, carbamoyl, acyl, haloacyl, alkylsulphinyl, alkylsulphonyl, haloalkylsulphinyl, haloalkylsulphonyl or sulphamoyl; provided that at least one of $R_1$ to $R_9$ is haloalkyl, haloalkylthio, haloalkylsulphinyl or haloalkylsulphonyl;

$R_{10}$ is hydrogen, alkyl, cycloalkyl, haloalkyl, alkoxy, alkoxyalkyl, haloalkoxyalkyl, alkylthioalkyl, haloalkylthioalkyl, alkenyl, alkinyl, alkoxycarbonyl, alkylthiocarbonyl, alkylthiothiocarbonyl, acylamino, diacylamino, dialkylamino, polymethylene-imino, polymethylene-imino interrupted by a heteroatom, unsubstituted or substituted benzyl or unsubstituted or substituted aryl;

$R_{11}$ is hydrogen or alkyl; and

Y is oxygen or sulphur;

are useful in treating coccidiosis in humans and animals.

29 Claims, No Drawings

1-(4-PHENOXY-PHENYL)-1,3,5-TRIAZINES

The present invention is concerned with 1-(4-phenoxy-phenyl)-1,3,5-triazines, a process for their production, pharmaceutical compositions useful for treating protozoan infections, and particularly coccidiosis, and methods of treating protozoan infections, and particularly coccidiosis, which embodies administering said compounds to humans or animals in need thereof.

It is known in the art that 2-(4-phenylthiophenyl)-2H,4H)-diones, 2-(4-phenylsulphinyl-phenyl)-(2H,4H)-diones and 2-(4-phenylsulphonyl)-phenyl)-1,2,4-triazine-3,5(2H,4H)-diones are useful for treating coccidiosis. (See Belgian Pat. Nos. 740,403 and 773,583.) However, these compounds are only disclosed as having activity against coccidiosis in poultry.

According to the present invention 1-(4-phenoxy-phenyl)-1,3,5-triazine derivatives of the formula

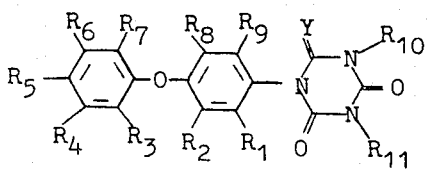

(I)

and pharmaceutically-acceptable, nontoxic salts thereof, wherein $R_1$, $R_2$, $R_3$, $R_4$, $R_5$, $R_6$, $R_7$, $R_8$ and $R_9$ are the same or different and each is hydrogen, straight- or branched-chain alkyl, especially lower alkyl, haloalkyl, especially halo(lower alkyl), alkoxy, especially lower alkoxy, haloalkoxy, especially halo(lower alkoxy), alkylthio, especially lower alkylthio, haloalkylthio, especially halo(lower alkylthio), halo, nitro, cyano, amino, acylamino, especially lower acylamino, alkoxycarbonylamino, especially lower alkoxycarbonylamino, carboxy, alkoxycarbonyl, especially lower alkoxycarbonyl, carbamoyl, acyl, especially lower acyl, haloacyl, especially halo(lower acyl), alkylsulphinyl, especially lower alkylsulphinyl, alkylsulphonyl, especially lower alkylsulphonyl, haloalkylsulphinyl, especially halo(lower alkylsulphinyl), haloalkylsulphonyl, especially halo(lower alkylsulphonyl) or sulphamoyl; provided that at least one of $R_1$ to $R_9$ is said haloalkyl, haloalkylthio, haloalkylsulphinyl or haloalkylsulphonyl;

$R_{10}$ is hydrogen, straight- or branched-chain alkyl, especially of 1 to 12 carbon atoms, cycloalkyl, especially of 4 to 7 carbon atoms, haloalkyl, especially halo(lower alkyl), alkoxy, especially lower alkoxy, alkoxyalkyl, especially (lower alkoxy)(lower alkyl), haloalkoxyalkyl, especially halo(lower alkoxy)(lower alkyl), alkylthioalkyl, especially (lower alkyl)thio(lower alkyl), haloalkylthioalkyl, especially halo(lower alkyl)thio(lower alkyl), alkenyl, especially lower alkenyl, alkinyl, especially lower alkinyl, alkoxycarbonyl, especially lower alkoxycarbonyl, alkylthiocarbonyl, especially lower alkylthiocarbonyl, alkylthiothiocarbonyl, especially lower alkylthiothiocarbonyl, acylamino, especially lower acylamino, diacylamino, especially di(lower acyl)amino, dialkylamino, especially di(lower alkyl)amino, polymethylene, polymethylene interrupted by a heteroatom, i.e., N, S or O, benzyl unsubstituted or substituted, preferably unsubstituted, or aryl, unsubstituted or substituted, preferably phenyl;

$R_{11}$ is hydrogen or alkyl, especially lower alkyl; and

Y is oxygen or sulphur; are produced which are particularly useful for their activity against coccidiosis in humans and animals.

The 1-(4-phenoxy-phenyl)-1,3,5-triazines of formula (I) and their salts may be prepared by a. reacting a compound of the formula:

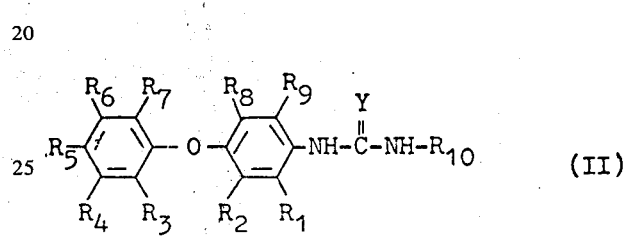

(II)

wherein $R_1$, $R_2$, $R_3$, $R_4$, $R_5$, $R_6$, $R_7$, $R_8$, $R_9$, $R_{10}$ and Y are as above defined, with a compound of the formula

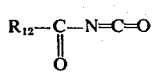

(III)

wherein $R_{12}$ is halo, lower alkoxy or monoaryloxy, to form a 1,3,5-triazine of the formula

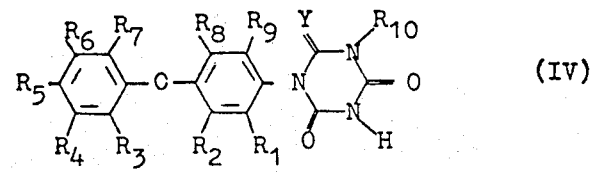

(IV)

wherein $R_1$, $R_2$, $R_3$, $R_4$, $R_5$, $R_6$, $R_7$, $R_8$, $R_9$, $R_{10}$ and Y are as above defined, isolating said compound, if desired, and reacting said compound either with or without acylation, if desired, with an alkylating agent of the formula

(V)

wherein

A is alkyl, n is 1, 2 or 3, and

Z is a moiety which easily forms an anion and, together with the acid hydrogen of the imino group of the compound of formula (IV), forms the molecule (H)$_n$Z, and in the case of the salts, reacting the compound produced with a suitable salt-forming moiety; or b. when at least one of R$_1$ to R$_9$ is said haloalkylsulphinyl or said haloalkylsulphonyl, reacting a compound of formula (I) wherein R$_1$, R$_2$, R$_3$, R$_4$, R$_5$, R$_6$, R$_7$, R$_8$ and R$_9$ are the same or different and each hydrogen, lower alkyl, halo(lower alkyl), lower alkoxy, halo(lower alkoxy), lower alkylthio, halo(lower alkylthio), halo, nitro, cyano, amino, lower acylamino, lower alkoxycarbonylamino, carboxy, lower alkoxycarbonyl, carbamoyl, lower acyl, halo(lower acyl), lower alkylsulphinyl, lower alkylsulphonyl, halo(lower alkylsulphinyl), halo(lower alkylsulphonyl) or sulphamoyl; provided that at least one of R$_1$ to R$_9$ is halo(lower alkylthio); and R$_{10}$, R$_{11}$ and Y are as above defined; with an oxidizing agent, and in the case of the salts reacting the compound produced with a suitable saltforming moiety, and recovering the compound produced.

It is to be considered surprising that the 1-(4-phenoxy-phenyl)-1,3,5-triazines of the formula (I) exhibit a far better activity against poultry coccidiosis E. tenella than commercially available compounds such as 3,5-dinitro-toluylamide, 1[(4-amino-2-propyl-5-pyrimidinyl)-methyl]-2-picolinium chloride hydrochloride, 3,5-dichloro-2,6-dimethylpyridone-4 and the complex of 4,4'-di-(nitrophenyl)-urea and 4,6-dimethyl-2-hydroxy-pyrimidine.

In addition, the compounds of the present invention are active against coccidiosis in humans as well as in poultry and this spectrum of activity is not known from the commercially available compounds used in the treatment of poultry coccidiosis.

If, in process variant (a), N-(3,5-dichloro-4-(4'-trifluoromethylthio-phenoxy)-phenyl)-N'-methyl-urea and chlorocarbonyl isocyanate are used as starting materials and methyliodide is used as the alkylating agent, the course of the reaction can be represented by the following equation:

If, in process variant (b), 1-(4-(4'-trifluoromethylthio-phenoxy)-phenyl)-3-ethyl-1,3,5-triazine-2,4,6-(1H,3H,5H)-trione and hydrogen peroxide are used as starting materials, the course of the reaction can be represented by the following equation:

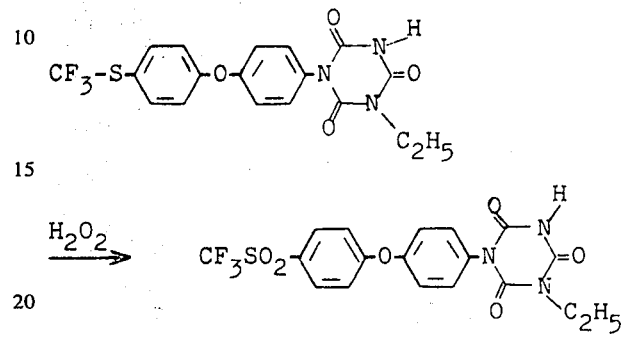

According to one embodiment of the present invention

R$_1$, R$_2$, R$_3$, R$_4$, R$_5$, R$_6$, R$_7$, R$_8$ and R$_9$ are the same or different and each is hydrogen, alkyl of 1 to 4 carbon atoms, alkoxy of 1 to 4 carbon atoms, alkylthio of 1 to 4 carbon atoms, trifluoromethyl, chloro, bromo, nitro, cyano, amino, acylamino of 1 to 4 carbon atoms, alkoxycarbonylamino of 1 to 4 carbon atoms in the alkoxy moiety, carboxyl, alkoxycarbonyl of 1 to 4 carbon atoms in the alkoxy moiety, carbamoyl, acyl of 1 to 5 carbon atoms, haloacyl of 1 to 3 halo atoms and 1 to 5 carbon atoms in the acyl moiety, alkylsulphonyl of 1 to 4 carbon atoms, haloalkoxy of 1 to 3 halogen atoms and 1 to 4 carbon atoms in the alkoxy moiety, haloalkylthio of 1 to 5 halogen atoms and 1 to 4 carbon atoms in the alkyl moiety, haloalkylsulphinyl of 1 to 7 halogen atoms and 1 to 4 carbon atoms in the alkyl moiety, or haloalkylsulphonyl of 1 to 7 halogen atoms and 1 to 4 carbon atoms in the alkyl moiety; provided that at least one of R$_1$ through R$_9$ is said haloalkoxy, haloalkylthio, haloalkylsulphinyl, or haloalkylsulphonyl; and

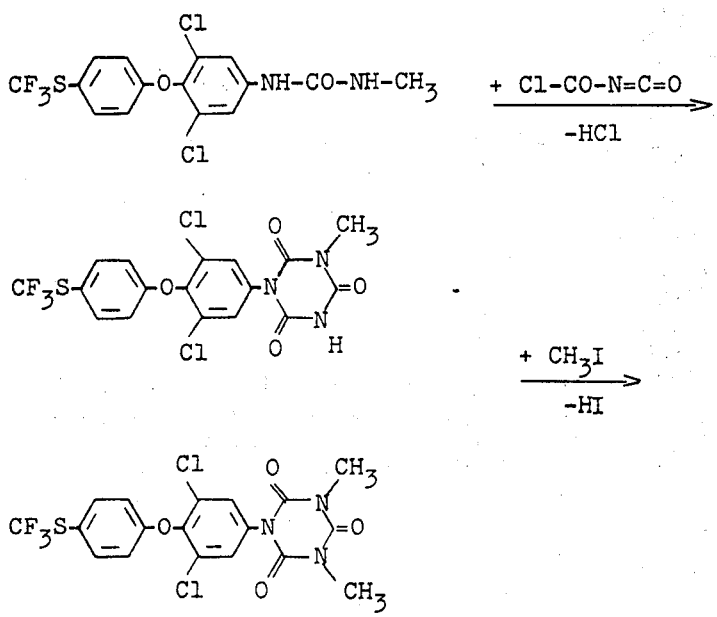

$R_{10}$ is hydrogen, straight-chain alkyl of 1 to 12 carbon atoms, branched-chain alkyl of 3 to 5 carbon atoms, chloroalkyl of 1 to 6 carbon atoms, alkoxy of 1 to 6 carbon atoms, alkoxyalkyl of 1 to 6 carbon atoms, haloalkoxyalkyl of 1 to 3 halogen atoms and 1 to 6 carbon atoms, alkenyl of 2 to 4 carbon atoms, alkinyl of 2 to 4 carbon atoms, alkoxycarbonyl of 1 to 4 carbon atoms, alkylthiocarbonyl of 1 to 4 carbon atoms, dialkylamino wherein each alkyl moiety is the same alkyl moiety of 1 to 4 carbon atoms, acylamino of 1 to 5 carbon atoms, diacylamino of 1 to 5 carbon atoms in each acyl moiety, polymethyleneimino, polymethyleneimino interrupted by 1 oxygen atom, phenyl or halophenyl.

According to another embodiment of the present invention $R_1$, $R_2$, $R_3$, $R_4$, $R_5$, $R_6$, $R_7$, $R_8$ and $R_9$ are the same or different and each is hydrogen, alkyl of 1 to 4 carbon atoms, alkoxy of 1 to 4 carbon atoms, alkylthio of 1 to 4 carbon atoms, trifluoromethyl, chloro, bromo, nitro, cyano, amino, acylamino of 1 to 4 carbon atoms, alkoxycarbonylamino of 1 to 4 carbon atoms in the alkoxy moiety, carboxyl, alkoxycarbonyl of 1 to 4 carbon atoms in the alkoxy moiety, carbamoyl, acyl of 1 to 4 carbon atoms, trifluoroacetyl, alkylsulphonyl of 1 to 4 carbon atoms, trifluoromethoxy, trifluoromethylthio, trifluoromethylsulphinyl, trifluoromethylsulphonyl; provided that at least one of $R_1$ through $R_9$ is trifluoromethoxy, trifluoromethylthio, trifluoromethylsulphinyl, or trifluoromethylsulphonyl; and $R_{10}$ is hydrogen, straight-chain alkyl of 1 to 12 carbon atoms, branched-chain alkyl of 3 to 5 carbon atoms, chloroalkyl of 1 to 6 carbon atoms, alkoxy of 1 to 6 carbon atoms, alkoxyalkyl of 1 to 6 carbon atoms, trifluoromethoxymethyl, alkenyl of 2 to 4 carbon atoms, alkinyl of 2 to 4 carbon atoms, alkoxycarbonyl of 1 to 4 carbon atoms, alkylthiocarbonyl of 1 to 4 carbon atoms, dialkylamino wherein each alkyl moiety is the same alkyl moiety of 1 to 4 carbon atoms, acylamino of 1 to 5 carbon atoms, phthalimido, succinimido, polymethyleneimino, polymethyleneimino interrupted by 1 oxygen atom, phenyl or halophenyl.

According to another embodiment of the present invention $R_1$, $R_2$, $R_3$, $R_4$, $R_5$, $R_6$, $R_7$, $R_8$ and $R_9$ are the same or different and each is hydrogen, alkyl of 1 or 2 carbon atoms, trifluoroalkyl of 1 or 2 carbon atoms, alkoxy of 1 or 2 carbon atoms, trifluoroalkoxy of 1 or 2 carbon, alkylthio of 1 or 2 carbon atoms, trifluoroalkylthio of 1 to 2 carbon atoms, chloro, bromo, nitro, cyano, alkylsulphonyl of 1 or 2 carbon atoms, trifluoroalkylsulphinyl of 1 or 2 carbon atoms, or trifluoroalkylsulphonyl of 1 or 2 carbon atoms; provided that at least 1 of $R_1$ through $R_9$ is said trifluoroalkyl, trifluoroalkylthio, trifluoroalkylsulphinyl, or trifluoroalkylsulphonyl;

$R_{10}$ is hydrogen, alkyl of 1 or 2 carbon atoms, alkenyl of 2 or 3 carbon atoms, alkoxycarbonyl of 1 or 2 carbon atoms in the alkyl moiety, dialkylamino wherein the alkyl moieties are the same and each are alkyl of 1 or 2 carbon atoms, phthalimido or alkoxy of 1 or 2 carbon atoms;

$R_{11}$ is hydrogen or alkyl of 1 to 3 carbon atoms; and Y is oxygen.

According to another embodiment of the present invention $R_1$, $R_2$, $R_3$, $R_4$, $R_5$, $R_6$, $R_7$, $R_8$ and $R_9$ are the same or different and each is hydrogen, methyl, methoxy, trifluoromethoxy, trifluoromethylthio, chloro, bromo, nitro, cyano, methylsulphonyl, trifluoromethylsulphinyl or trifluoromethylsulphonyl; provided that at least one of $R_1$ to $R_9$ is trifluoromethylthio, trifluoromethylsulphinyl, or trifluoroalkylsulphonyl;

$R_{10}$ is hydrogen, methyl, methoxy, methoxycarbonyl, allyl, dimethylamino or phthalimido; and Y is oxygen.

According to another embodiment of the present invention $R_1$, $R_2$, $R_8$ and $R_9$ are each selected from the group consisting of hydrogen, methyl, chloro, bromo, and trifluoromethylthio;

$R_3$, $R_4$, $R_5$, $R_6$ and $R_7$ are each selected from the group consisting of hydrogen, methyl, methoxy, trifluoromethoxy, trifluoromethylthio, chloro, bromo, nitro, cyano, methylsulphonyl, trifluoromethylsulphinyl, and trifluoromethylsulphonyl; provided that at least one of $R_1$ to $R_9$ is trifluoromethylthio, trifluoromethylsulphinyl, or trifluoromethylsulphonyl;

$R_{10}$ is hydrogen, methyl, methoxy, methoxycarbonyl, allyl, dimethylamino, or phthalimido; and Y is oxygen.

According to another embodiment of the present invention $R_1$, $R_2$, $R_3$, $R_4$, $R_5$, $R_6$, $R_7$, $R_8$ and $R_9$ are the same or different and each is hydrogen, alkyl of 1 or 2 carbon atoms, trifluoroalkoxy of 1 or 2 carbon atoms, trifluoroalkylthio of 1 or 2 carbon atoms in the alkyl moiety, tetrafluoroalkylthio of 2 carbon atoms in the alkyl moiety, chloro, bromo, trifluoroalkylsulphonyl of 1 or 2 carbon atoms or tetrafluoroalkylsulfonyl of 2 carbon atoms; provided that at least 1 of $R_1$ through $R_9$ is trifluoroalkylthio of 1 or 2 carbon atoms, tetrafluoroalkylthio of 2 carbon atoms, trifluoroalkylsulphonyl of 1 or 2 carbon atoms or tetrafluoroalkylsulfonyl of 2 carbon atoms;

$R_{10}$ is hydrogen or alkyl of 1 or 2 carbon atoms;
$R_{11}$ is alkyl of 1 or 2 carbon atoms; and
Y is oxygen.

According to another embodiment of the present invention $R_1$, $R_2$, $R_3$, $R_4$, $R_5$, $R_6$, $R_7$, $R_8$ and $R_9$ are the same or different and each is hydrogen, methyl, trifluoromethoxy, trifluoromethylthio, tetrafluoroethylthio, chloro, bromo or trifluoromethylsulphonyl; provided that at least one of $R_1$ through $R_9$ is trifluoromethylthio, tetrafluoroethylthio trifluoromethylsulphonyl; or tetrafluoroethylsulfonyl;

$R_{10}$ is hydrogen or methyl;
$R_{11}$ is methyl or ethyl; and
Y is oxygen.

According to another embodiment of the present invention $R_1$, $R_3$, $R_4$, $R_7$ and $R_9$ are each hydrogen;
$R_2$ is hydrogen, methyl, chloro or bromo;
$R_5$ is trifluoromethoxy, trifluoromethylthio, tetrafluoroethylthio, trifluoromethylsulphonyl or tetrafluoroethylsulfonyl;
$R_6$ is hydrogen or methyl;
$R_8$ is hydrogen, methyl, chloro or bromo;
$R_{10}$ is hydrogen or methyl;
$R_{11}$ is methyl or ethyl; and
Y is oxygen.

$R_{12}$ preferably is chloro, methoxy or phenoxy; Z is preferably halo, especially chlorine, bromine or iodine, or $SO_4$, and A is preferably alkyl of 1 to 4 carbon atoms.

The substituted ureas and thioureas used as starting materials are largely unknown but can be prepared according to known methods, by (a) either reacting substituted 4-aminodiphenylethers with the appropriate substituted isocyanates or isothiocyanates in inert organic solvents, if necessary in the presence of tertiary bases such as triethylamine, pyridine and others, at temperatures between 0° and 100°C, or on converse sequence, b. reacting substituted amines with the appropriate substituted 4-isocyanato- or 4-isothiocyanato-diphenylethers under the same conditions, or by c. condensing substituted p-aminophenolureas with activated halogeno-aromatic compounds in aprotic solvents such as dimethylsulphoxide, dimethylformamide or hexamethylphosphoric acid triamide in the presence of bases such as sodium hydride, potassium hydroxide, potassium carbonate and others at temperatures between 20°C and 150°C.

If the amount of solvent is chosen appropriately, the reaction products as a rule crystallize out on cooling the solution. Literature on the alternative preparation of ureas from amines and isocyanates: *Methoden der Org. Chemie* (Methods of Organic Chemistry), (Houben-Weyl), 4th edition, volume VIII, pages 157–158.

Representative starting materials of formula (II) which may be used according to the above-described process include: N-[3,5-dichloro-4-(4′-trifluoromethylthio-phenoxy)-phenyl]-urea, N-[3,5-dichloro-4-(3′-bromo-4′-trifluoromethoxy-phenoxy)-phenyl]-N′-propyl-urea, N-[3,5-dimethyl-4-(3′-trifluoromethylthio-phenoxy)-phenyl]-N′-methyl-urea, N-[3-chloro-4-(4′-trifluoromethylthio-phenoxy)phenyl]-N′-methyl-urea, N-[3-trifluoromethylthio-4-(4′-cyanophenoxy)-phenyl]-N′-allyl-urea, N-[4-(2′-nitro-4′-trifluoromethylthio-phenoxy)-phenyl]-N′-methyl-urea, N-[4-(2′-trifluoromethylthio-4′-methoxy-phenoxy)-phenyl]-N′-dimethylamino-urea, N-[3-trifluoromethylthio-4-(4′-methylthio-phenoxy)-phenyl]-N′-phthalimido-urea, N-[2-methyl-4-(3′-methyl-4′-trifluoromethylthio-phenoxy)-phenyl]-N′-methoxy-urea, N-[3,5-dichloro-4-(2′- -methyl-4′-trifluoromethylthio-phenoxy)-phenyl]-N′-methyl-urea, N-[3-chloro-5-methyl-4-(2′-chloro-4′-trifluoromethylthio-phenoxy)-phenyl]-N′-methyl-urea, N-[3,5-dimethyl-4-(4′-trifluoromethylthio-phenoxy)-phenyl]-N′-methyl-urea, N-[3-chloro-5-methyl-4-(4′-trifluoromethylthio-phenoxy)-phenyl]-N′-methyl-urea, N-[3-chloro-4-(2′-chloro-4′-trifluoromethylthio-phenoxy)-phenyl]-N′-methyl-urea, N-[3-bromo-4-(4′-trifluoromethylthio-phenoxy)-phenyl]-N′-methyl-urea, N-[3-chloro-5-trifluoromethyl]-4-(4′-trifluoromethylthio-phenoxy)-phenyl]-N′-methyl-urea and N-[3,5-dichloro-4-(4′-trifluoromethylsulphonyl-phenoxy)-phenyl]-N′-methyl-thiourea.

Diluents which can be used both for the reaction of the ureas or thioureas of the formula II with carbonylisocyanates of the formula III and for the reaction of the 1,3,5-triazine derivatives of the formula IV with compounds of the formula (A)$_n$-Z are all organic solvents which are inert to this reaction. These include, in addition to pyridine, preferably aromatic hydrocarbons such as benzene, toluene and xylene, halogenated aromatic hydrocarbons such as chlorobenzene or dichlorobenzene and ethers, such as tetrahydrofurane and dioxane.

The hydrochloric acid which is produced in the reaction (if $R_{12}$ is chloro) is evolved as a gas or can be bound by organic or inorganic acid acceptors. The acid acceptors preferably include tertiary organic bases such as triethylamine, pyridine and others, or inorganic bases such as alkali metal carbonates or alkaline earth metal carbonates.

For both the above-mentioned reaction stages, the reaction temperatures can be varied over a large range. In general, the reaction is carried out between about 0°C and about 150°C, preferably between 20°C and 100°C.

The reactions according to the above processes may be carried out at atmospheric pressure or superatmospheric pressure. Atmospheric pressure is preferred.

According to the processes above described, the reactants are preferably used in equimolar amounts.

The following compounds are representative of oxidizing agents which may be used to convert the haloalkylthio compounds, such as the trifluoromethylthio compounds of the formula (I) wherein Y is oxygen, into the corresponding sulphinyl or sulphonyl compounds: $H_2O_2$/glacial acetic acid; $H_2O_2$/acetic anhydride; $H_2O_2$/methanol; peracids, such as, for example, m-chloroperbenzoic acid; chromic acid; potassium permanganate; sodium periodate; cerium ammonium nitrate; nitric acid.

The following compounds are representative of those of the present invention:

1-[4-(4′-trifluoromethoxy-phenoxy)-phenyl]-3-ethyl-1,3,5-triazine-2,4,6(1H, 3H, 5H)-trione, 1-[3,5-dichloro-4-(4′-trifluoromethoxy-phenoxy)-phenyl]-3-methyl-1,3,5-triazine-2,4,6(1H, 3H, 5H)-trione, 1-[3,5-dichloro-4-(4′-trifluoromethylthio-phenoxy)-phenyl]-3-methyl-1,3,5-triazine-2,4,6(1H, 3H, 5H)-trione, 1-[4-(4′-trifluoromethylthio-phenoxy)-phenyl]-3-ethyl-1,3,5-triazine-2,4,6(1H, 3H, 6H)-trione, 1-[4-(4′-trifluoromethylthio-phenoxy)-phenyl]-3-methyl-1,3,5-triazine-2,4,6(1H, 3H, 5H)-trione, 1-[3,5-dichloro-4-(4′-trifluoromethylthio-phenoxy)-phenyl]-3-ethyl-1,3,5-triazine-2,4,6(1H, 3H, 5H)-trione, 1-[3-chloro-5-bromo-4-(4′-trifluoromethylthio-phenoxy)-phenyl]-3-methyl-1,3,5-triazine-2,4,6 (1H, 3H, 5H)-trione, 1-[3,5-dibromo-4-(4′-trifluoromethylthio-phenoxy)-phenyl]-3-methyl-1,3,5-triazine-2,4,6(1H, 3H, 5H)-trione, 1-[3,5-dichloro-4-(3′-methyl-4′-trifluoromethylthio-phenoxy)-phenyl]-3-methyl-1,3,5-triazine-2,4,6(1H, 3H, 5H)-trione, 1-[3,5-dichloro-4-(4′-trifluoromethylthio-phenoxy)-phenyl]-3,5-dimethyl-1,3,5-triazine-2,4,6(1H, 3H, 5H)-trione, 1-[4-(4′-trifluoromethylsulphonyl-phenoxy)-phenyl]-3-ethyl-1,3,5-triazine-2,4,6(1H, 3H 5H)-trione, 1-[4-(4′-trifluoromethylsulphonyl-phenoxy)-phenyl]-3-methyl-1,3,5-triazine-2,4,6(1H, 3H, 5H)-trione, 1-[3,5-dichloro-4-(4′-trifluoromethylsulphonyl-phenoxy)-phenyl]-3-methyl-1,3,5-triazine-2,4,6(1H, 3H, 5H)-trione, 1-[3,5-dichloro-4-(4′-trifluoromethylsulphonyl-phenoxy)-phenyl]-3-ethyl-1,3,5-triazine-2,4,6(1H, 3H, 5H)-trione, 1-[3,5-dichloro-4-(4′-trifluoromethylsulphonyl-phenoxy)-phenyl]-3,5-dimethyl-1,3,5-triazine-2,4,6(1H, 3H, 5H)-trione, 1-[3-chloro-5-bromo-4-(4′-trifluoromethylsulphonyl-phenoxy)-phenyl]-3-methyl-1,3,5-triazine-2,4,6(1H, 3 H, 5H)-trione, 1-[3,5-dichloro-4-(4′-methyl-4′-trifluoromethylsulphonyl-phenoxy)-phenyl]-3-methyl-1,3,5-triazine-2,4,6(1H, 3H, 5H)-trione, 1-[3,5-dichloro-4-(4′-trifluoromethylsulphonyl-phenoxy)-phenyl]-1,3,5-triazine-2,4,6(1H, 3H, 5H)-trione, 1-[3,5-dichloro-4-(2'-chloro-4'-trifluoromethylsulphonyl-phenoxy)-phenyl]-3-methyl-1,3,5-triazine-2,4,6(1H, 3H, 5H)-trione, 1-[3,5-dichloro-4-(3'-bromo-4-trifluoromethoxy-phenoxy)-phenyl]-3-propyl-1,3,5-triazine-2,4,6(1H, 3H, 5H)-trione, 1-[4-(4'-trifluoromethylsulphinyl-phenoxy)-phenyl]-3-methyl-1,3,5-triazine-2,4,6(1H, 3H, 5H)-trione, 1-[3,5-dichloro-4-(4'-trifluoromethylsulphinyl-phenoxy)-phenyl]-3-methyl-1,3,5-triazine, 2,4,6(1H, 3H, 5H)-trione, 1-[4-(3'-trifluoromethylsulphonyl-phenoxy)-3,5-dimethyl-phenyl]-3-methyl-1,3,5-triazine-2,4,6(1H, 3H, 5H)-trione, 1-[3-chloro-4-(4'-trifluoromethylsulphonyl-phenoxy)-phenyl]-3-methyl-1,3,5-triazine-2,4,6(1H, 3H, 5H)-trione, 1-[3-trifluoromethylthio-4-(4'-cyanophenoxy)-phenyl]-5-allyl-1,3,5-triazine-2,4,6(1H, 3H, 5H)-trione, 1-[4-(2'-nitro-4'-trifluoromethylsulphonyl-phenoxy)-phenyl]-3-methyl-5-methoxycarbonyl-1,3,5-triazine-2,4,6(1H, 3H, 5H)-trione, 1-[4-(2'-trifluoromethylthio-4'-methoxy-phenoxy)-phenyl]-5-dimethylamino-1,3,5-triazine-2,4,6(1H, 3H, 5H)-trione, 1-[3-trifluoromethylsulphonyl-(4'-methylsulphonylphenoxy)-phenyl]-5-phthalimido-1,3,5-triazine-2,4,6(1H, 3H, 5H)-trione, 1-[2-methyl-4-(3'-methyl-4'-trifluoromethylthio-phenoxy)-phenyl]-5-methoxy-1,3,5-triazine-2,4,6(1H, 3H, 5H)-trione, 1-[3,5-dichloro-4-(2'-methyl-4'-trifluoromethylsulphonyl-phenoxy)-phenyl]-3-methyl-1,3,5-triazine12,4,6(1H, 3H, 5H)-trione, 1-[3-chloro-5-methyl-4-(2'-chloro-4'-trifluoromethylsulphonyl-phenoxy)-phenyl]-3-methyl-1,3,5-triazine-2,4,6(1H, 3H, 5H)-trione, 1-[4-(4'-trifluoromethylsulphonyl-phenoxy)-3,5-dimethyl-phenyl]-3-methyl-1,3,5-triazine-2,4,6(1H, 3H, 5H)-trione, 1-[3-chloro-5-methyl-4-(4'-trifluoromethylsulphonyl-phenoxy)-phenyl]-3-methyl-1,3,5-triazine-2,4,6(1H, 3H, 5H)-trione, 1-[3-chloro-4-(2'-chloro-4'-trifluoromethylthio-phenoxy)-phenyl]-3-methyl-1,3,5-triazine-2,4,6(1H, 3H, 5H)-trione, 1-[3-bromo-4-(4'-trifluoromethylsulphonyl-phenoxy)-phenyl]-3-methyl-1,3,5-triazine-2,4,6(1H, 3H, 5H)-trione, 1-[3-chloro-5-trifluoromethyl-4-(4'-trifluoromethylsulphonyl-phenoxy)-phenyl]-3-methyl-1,3,5-triazine-2,4,6(1H, 3H, 5H)-trione and 1-[3,5-dichloro-4-(4'-trifluoromethylsulphonyl-phenoxy)-phenyl]-3-methyl-2-thioxo-3,5-1,3,5(1H, 3H, 5H)-triazine.

The compounds of this invention and their salts exhibit powerful coccidiocidal effects. They are highly active against the species of coccidia of poultry, such as, for example, *Eimeria tenella* (coccidiosis of the appendix in chickens), *E. acervulina*, *E. brunetti*, *E. maxima*, *E. mitis*, *E. mivati*, *E. necatrix* and *E. praecos* (coccidiosis of the small intestine in chickens), and can accordingly be used for the prophylaxis and treatment of coccidiosis infections of poultry. In addition, the new active compounds are distinguished by a very powerful activity in coccidial infections of other animals, particularly mammals, such as, for example, of rabbits such as *E. stiedae* (coccidiosis of the liver), *E. magna*, *E. media*, *E. irresidua* and *E. perforans* (coccidiosis of the intestine), of sheep, cattle and other domestic animals, including dogs and cats, and of laboratory animals such as white mice (*E. falciformis*) and rats.

In addition, the compounds have activity against toxoplasmosis and can be employed both for the treatment of the cats which excrete the infectious stages (oocysts) and for the treatment of the infected humans.

Coccidial infections can lead to severe losses in the case of domestic animals and represent a significant problem, especially in raising poultry and mammals such as cattle, sheep, rabbits and dogs. The action of the previously known agents against coccidiosis in poultry is, in most cases, restricted to but a few species. The treatment and prophylaxis of coccidiosis in mammals hitherto represents a largely unsolved problem.

The compounds of this invention can be administered to livestock in a variety of formulations, such as in premixes for administration with the feed, in drinking water, and in pour-on formulations. While the compounds are, as a rule, most suitably administered in this fashion, namely with the feed or in the drinking water, the compounds can also be administered to individual animals in the form of tablets, medicinal drinks, capsules or the like, or by injection. These last-mentioned methods of administration are, of course, less suitable for the treatment of a large number of animals than for the treatment of a limited number of animals; however, they are very suitable for administration to a small number of animals or to individual animals.

The present invention thus includes compositions containing the 1-(4-phenoxy-phenyl)-1,3,5-triazine and a carrier. This includes a medicated fodder comprising the compound and a nutritious material. Medicated fodder according to the present invention is usually prepared by thoroughly mixing about 5 to 5000 ppm of active compound with a nutritionally balanced feed. In the treatment and prophylaxis of coccidiosis of poultry suitable dosages are obtained by admixture of 5–250 ppm, preferably 10–100 ppm, to the feed, for example, with the chick feed described below.

To prepare a concentrate of a premix which is intended for ultimate dilution with the feed to the above-mentioned values, generally about 1% to 30%, preferably about 10% to 20% by weight, of active compound are mixed with an edible organic or inorganic excipient, as for example corn flour, a mixture of corn and soya bean meal or mineral salts which contain a small amount of an edible dust-suppressant oil, for example corn oil or soya bean oil. The premix is then added to an otherwise complete feed before the latter is made available to the livestock. The following composition is an example of the use of the compounds according to the invention in poultry feed:

| | |
|---|---|
| 52.000% | of shredded cereal feed |
| 17.9975% | of shredded soya |
| 5.000% | of corn gluten feed |
| 5.000% | of wheat wholemeal |
| 3.000% | of fish meal |
| 3.000% | of tapioca meal |
| 3.000% | of green lucerne meal |
| 2.000% | of comminuted wheat germ |
| 2.000% | of soya oil |
| 1.600% | of fishbone meal |
| 1.500% | of whey powder |
| 1.400% | of carbonated feed lime |
| 1.000% | of feed line phosphate |
| 1.000% | of molasses |
| 0.500% | of brewer's yeast |
| 0.0025% | of 1-[3,5-dichloro-4-(4'-trifluoromethyl-sulphonyl-phenoxy)-phenyl]-3-methyl, 1,3,5-triazine-2,4,6(1H, 3H, 5H)-trione |
| 100.0000% | |

Such a feed is suitable both for curative and for prophylactic use.

In the mass treatment and prophylaxis of coccidiosis of poultry, above all of coccidiosis of chickens, ducks, geese and turkeys, suitable dosages in practice are obtained by admixture of 5 to 250 ppm, preferably 10 to 100 ppm, to the feed; in special cases, because of good toleration, these amounts can be increased. A lowering of the dose can be achieved by combination with imidazole-4,5-dicarboxylic acid amide or sulphonamides, such as, for example, the p-aminobenzenesulphonamides of 2-amino-4,6-dimethylpyrimidine, of 2-aminoquinoxaline, of 2-amino-5-methoxypyrimidine and of 2-amino-4-methyl-pyrimidine, because these boost the activity. On an individual treatment basis, generally a dose of from 5 to 250 mg/kg of body weight is administered, which may be divided between several administrations.

The coccidiocidal activity of compounds representative of those of the present invention is set forth in Tables 1 and 2 below. *Eimeria tenella* (coccidiosis of the appendix in chickens) is given as an example of the activity against poultry coccidia and *Eimeria falciformis* (mice) is given as an example of a coccid in mammals.

changes in the appendices, which lead to severe haemorrhages. In testing the activity against *E. tenella*, the compounds according to this invention were administered with the feed from 3 days before infection to 9 days after infection (end of the experiment).

The number of oocysts was determined with the aid of the Mc-Master chamber (on this subject, see Engelbrecht et al., *Parasitologische Arbeitsmethoden in Medizin und Veterinärmedizin* (Parasitological procedures in Medicine and Veterinary Medicine), page 172, Akademie-Verlag Berlin (1965)).

The treatment of the *Eimeria falciformis* infection of mice, mentioned as an example of coccidia in mammals, took place on the 1st, 2nd, 3rd, 6th, 7th and 8th day after infection. The infection was brought about with 10,000 sporulated oocysts per mouse (weighing 15 g). In the case of the untreated controls, from the 7th day after infection onwards massive excretion of oocysts and diarrhoea containing blood are observed, and 30% of the animals die of the infection.

Table 1

Comparison of the effects of preparation examples Nos. 3 and 13 with those of 1-[(4-amino-2-propyl-5-pyrimidinyl)-methyl]-2-picolinium chloride hydrochloride (=P) of Eimeria tenella/chicks

| Criteria | Dose 50 ppm in the feed | | | 25 ppm in the feed | | | 10 ppm in the feed | | | Infected untreated control |
|---|---|---|---|---|---|---|---|---|---|---|
| | Preparation example No. 3 | | P | Preparation example No. 3 | | P | Preparation example No. 3 | | P | |
| | | 13 | | | 13 | | | 13 | | |
| Mortality rate | 0/3 | 0/3 | 0/5 | 0/6 | 0/9 | 0/6 | 0/3 | 0/12 | 1/3 | 2/6 |
| O ocyst excretion in % compared to the untreated infected control | 0.3% | 0 | 46% | 6% | 0.2% | 75% | 48% | 0.05% | 82% | 100 |
| Weight increase in % compared to the non-infected untreated control | 87% | 91% | 63% | 97% | 80% | 90% | 80% | 95% | 25% | 38 |
| Blood excretion with the faeces*) | 0 | 0 | + | + | 0 | ++ | +++ | 0 | ++ | +++ |
| Macroscopic dissection findings*) | 0 | 0 | ++ | ++ | 0 | ++ | ++ | 0 | +++ | +++ |

*the pathological changes caused by the infection, and the degree of excretion of blood, are coded as follows:
+++ = strong
++ = moderate
+ = slight
0 = no changes Table 2

Comparison of the effects of comparison examples Nos. 1, 2, 3, 12 and 13 with those of 1-[(4-amino-2-propyl-5-pyrimidinyl)-methyl]-2-picolinium chloride hydrochloride (=P) on a mammal coccid (Eimeria falciformis)

| Preparation example No. | Dose in mg/kg of body weight | | | | | | | | | |
|---|---|---|---|---|---|---|---|---|---|---|
| | 100 | 50 | 25 | 10 | 5 | 2.5 | 1 | 0.5 | 0.25 | 0.1 |
| 1 | 2 | 2 | 2 | 1 | 0 | | | | | |
| 2 | | | 2 | 2 | 2 | 2 | 2 | 2 | 1 | 0 |
| 3 | 2 | 2 | 2 | 2 | 2 | 2 | 1 | 0 | | |
| 12 | 2 | 2 | 2 | 2 | 1 | 0 | | | | |
| 13 | 2 | 2 | 2 | 2 | 2 | 2 | 1 | 0 | | |
| P | 0*) | | | | | | | | | |

*)500 mg/kg : 1
250 mg/kg : 0
Codes: 2 = effect
1 = slight effect
0 = no effect

If, for example, 11 day old chicks are infected with 30,000 sporulated occysts of *Eimeria tenella*, the pathogen of coccidiosis of the appendix, 30% to 70% of the animals die in the case of the untreated controls. The surviving chicks excrete 300,000 to 500,000 oocysts per gram (opg) of faeces daily from the 7th to the 9th day after the infection. In the course of the illness, the weight increase is considerably impaired and there are pronounced macroscopially detectable pathological The compounds of the present invention can also be used for the treatment of toxoplasmosis in humans. For this use, and for individual treatment of animals other than humans, the compounds are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing withh a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

The pharmaceutical compositions of the present invention contain a major or minor amount, e.g. 0.1% to 99.5%, preferably 0.5% to 90%, of active ingredient as above defined in combination with a pharmaceutically acceptable, nontoxic, inert, diluent or carrier, the carrier comprising one or more solid, semi-solid or liquid diluent, filler and formulation adjuvant which is nontoxic, inert and pharmaceutically-acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses, or alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage will be from 5 to 250 mg/kg of body weight per day. In some instances a sufficient therapeutic effect can be obtained at a lower dose, while in others a larger dose will be required.

While the routes of administration include oral, parenteral (i.e., intramuscular, intraperitoneal and intravenous), rectal, and topical, oral administration is particularly preferred.

The preferred pharmaceutical compositions are therefore those in a form suitable for oral administration such as tablets, pills, dragees, capsules and ampoules.

The following nonlimitative examples more particularly illustrate the present invention:

EXAMPLE 1

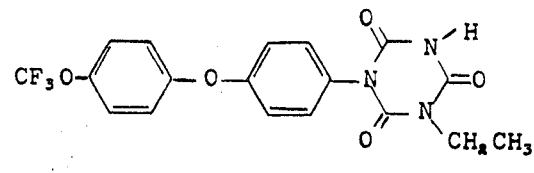

5 g (14.7 mmols) of N-[4-(4'-trifluoromethoxyphenoxy)-phenyl]-N'-ethyl-urea of melting point 154°–155°C are suspended in 50 ml of absolute toluene and 1.8 g. (17 mmols) of chlorocarbonyl isocyanate are added dropwise at 20°C while stirring. The mixture is then stirred for 1 hour at 20°C and 3 hours at the boil. When cold, it is concentrated in vacuo and the 1-[4-(4'-trifluoromethoxy-phenoxy)-phenyl]-3-ethyl-1,3,5-triazine-2,4,6(1H, 3H, 5H)-trione which has separated out is filtered off and purified by recrystallization from ethyl acetate/petroleum ether (1:1).

Melting point 176°–177°C yield 67% of theory.

The following compounds were prepared in an analogous manner from the reactants set forth:

| Example No. | |
|---|---|
| 2 | 1-[3,5-Dichloro-4-(4'-trifluoromethoxy-phenoxy)-phenyl]-3-methyl-1,3,5-triazine-2,4,6(1H,3H,5H)-trione, melting point 198°–199° C<br>From: N-[3,5-Dichloro-4-(4'-trifluoromethoxy-phenoxy)-phenyl]-N'-methyl-urea and chlorocarbonyl isocyanate. |
| 3 | 1-[3,5-Dichloro-4-(4'-trifluoromethylthio-phenoxy)-phenyl]-3-methyl-1,3,5-triazine-2,4,6(1H,3H,5H)-trione, melting point 235°C.<br>From: N-[3,5-Dichloro-4-(4'-trifluoromethyl-thiophenoxy)-phenyl]-N'-methyl-urea and chlorocarbonyl isocyanate |
| 4 | 1-[4-(4'-Trifluoromethylthio-phenoxy)-phenyl]-3-ethyl-1,3,5-triazine,2,4,6(1H,3H,5H)-trione, melting point 177°C.<br>From: N[4-(4'-Trifluoromethylthio-phenoxy)-phenyl]-N'-ethyl-urea and chlorocarbonyl isocyanate |
| 5 | 1-[4-(4'-Trifluoromethylthio-phenoxy)-phenyl]-3-methyl-1,3,5-triazine-2,4,6(1H,3H,5H)-trione, melting point 141° C.<br>From: N-[4-(4'-Trifluoromethylthio-phenoxy)-phenyl]-N'-methyl-urea and phenoxycarbonyl isocyanate |
| 6 | 1-[3,5-Dichloro-4-(4'-trifluoromethylthio-phenoxy)-phenyl]-3-ethyl-1,3,5-triazine-2,4,6(1H,3H,5H)-trione, melting point 196° C.<br>From: N-[3,5-Dichloro-4-(4'-trifluoromethylthio-phenoxy)-phenyl]-N'-ethyl-urea and chlorocarbonyl isocyanate |
| 7 | 1-[3-Chloro-5-bromo-4-(4'-trifluoromethylthio-phenoxy)-phenyl]-3-methyl-1,3,5-triazine-2,4,6(1H,3H,5H)-trione, melting point 217° C.<br>From: N-[3-Chloro-5-bromo-4-(4'-trifluoromethyl-thio-phenoxy)-phenyl]-N'-methyl-urea and methoxycarbonyl isocyanate |
| 8 | 1-[3,5-Dibromo-4-(4'-trifluoromethylthio-phenoxy)-phenyl]-3-methyl-1,3,5-triazine-2,4,6(1H,3H,5H)-trione, melting point 208° C.<br>From: N-[3,5-Dibromo-4-(4'-trifluoromethylthio-phenoxy)-phenyl]-N'-methyl-urea and chlorocarbonyl isocyanate. |
| 9 | 1-[3,5-Dichloro-4-(3'-methyl-4'-trifluoromethylthio-phenoxy)-phenyl]-3-methyl-1,3,5-triazine-2,4,6(1H,3H,5H)-trione, melting point 244° C.<br>From: N-[3,5-Dichloro-4-(3'methyl-4'-trifluoromethyl-thio-phenoxy)-phenyl]-N'-methyl-urea and chlorocarbonylisocyanate |
| 10 | 1-[3,5-Dichloro-4-(4'-(1,1,2,2-Tetrafluoromethyl-thio)-phenoxy)-phenyl]-3-methyl-1,3,5-triazine-2,4,6-(1H,=H,5H)-trione, melting point 195°C.<br>From: N-[3,5-Dichloro-4-(4'-1,1,2,2-Tetrafluoroethylthio)-phenoxy)-phenyl]-N'-methyl-urea and chlorocarbonyl isocyanate. |

EXAMPLE 11

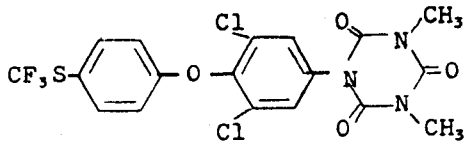

The dry residue from the reaction of an 0.05 molar sodium ethylate solution with 24 g (0.05 mol) of 1-[3,5-dichloro-4-(4'-trifluoromethylthio-phenoxy)-phenyl]-3-methyl-1,3,5-triazine-2,4,6(1H, 3H, 5H)-trione of melting point 235°C is dissolved in 100 ml of absolute dimethylformamide and 7.5 g (0.053 mol) of methyl iodide are added, while stirring. The mixture is stirred for 2 hours at 120°C, concentrated in vacuo and finally stirred with 200 ml of water. After filtration and drying, the 1-[3,5-dichloro-4-(4'-trifluoromethylthio-phenoxy)-phenyl]-3,5-dimethyl-1,3,5-triazine-2,4,6(1H, 3H, 5H)-trione is recrystallized from ethanol/water (7:3).

Melting point 141°C, yield 77% of theory.

EXAMPLE 12

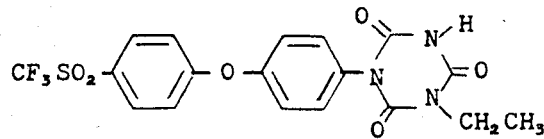

2.9 g (25 mmols) of 30% strength hydrogen peroxide are added dropwise to a solution of 3.5 g (8.3 mmols) of 1-[4-(4'-trifluoromethylthio-phenoxy)-phenyl]-3-ethyl-1,3,5-triazine-2,4,6(1H,3H,5H)-trione of melting point 177°C in 30 ml of anhydrous acetic acid at 20°C. The mixture is then stirred for a further 3 hours at 90°C, 150 ml of ice water are added and the product is filtered off. The 1-[4-(4'-trifluoromethylsulphonyl-phenoxy)-phenyl]-3-ethyl-1,3,5-triazine-2,4,6(1H,3H,5H)-trione is recrystallized from ethanol. Melting point 196°C, yield 66% of theory.

The following compounds were prepared in a manner analogous to that of Example 12 from the reactants set forth:

| Example No. | |
|---|---|
| 13 | 1-[4-(4'-Trifluoromethylsulphonyl-phenoxy)-phenyl]-3-methyl-1,3,5-triazine-2,4,6(1H,3H,5H)-trione, melting point 180° C.<br>From: 1-[4-(4'-Trifluoromethylthio-phenoxy)-phenyl]-3-methyl-1,3,5-triazine-2,4,6(1H,3H,5H)-trione and hydrogen peroxide |
| 14 | 1-[3,5-Dichloro-4-(4'-trifluoromethyl-sulphonyl-phenoxy)-phenyl]-3-methyl-1,3,5-triazine-2,4,6(1H,3H,5H)-trione, melting point 270°C.<br>From: 1-[1-[3,5-dichloro-4-(4'-trifluoromethyl-thio-phenoxy)-phenyl]-3-methyl-1,3,5-triazine-2,4,6(1H,3H,5H)-trione and peracetic acid |
| 15 | 1-[3,5-Dichloro-4-(4'-trifluoromethylsulphonyl-phenoxy)-phenyl]-3-ethyl-1,3,5-triazine-2,4,6-(1H,3H,5H)-trione, melting point 298° C.<br>From: 1-[3,5-Dichloro-4-(4'-trifluoromethylthio-phenoxy)-phenyl]-3-ethyl-1,3,5-triazine-2,4,6-(1H,3H,5H)-trione and hydrogen peroxide |
| 16 | 1-[3,5-Dichloro-4-(4'-trifluoromethylsulphonyl-phenoxy)-phenyl]-3,5-dimethyl-1,3,5-triazine-2,4,6(1H,3H,5H)-trione, melting pont 241° C.<br>From: 1-[3,5-Dichloro-4-(4'-trifluoromethylthio-phenoxy)-phenyl]-3,5-dimethyl-1,3,5-triazine-2,4,6(1H,3H,5H)-trione and hydrogen peroxide |
| 17 | 1-[3-Chloro-5-bromo-4-(4'-trifluoromethylsulphonyl-phenoxy)-phenyl]-3-methyl-1,3,5-triazine-2,4,6(1H,3H,5H)-trione, melting point 245° C.<br>From: 1-[3-Chloro-5-bromo-4-(4'-trifluoromethyl-thio-phenoxy)-phenyl]-3-methyl-1,3,5-triazine-2,4,6(1H,3H,5H)-trione and peracetic acid |
| 18 | 1-[3,5-Dibromo-4-(4'-trifluoromethylsulphonyl-phenoxy)-phenyl]-3-methyl-1,3,5-triazine-2,4,6(1H,3H,5H)-trione, melting point 248° C.<br>From: 1-[3,5-Dibromo-4-(4'-trifluoromethylthio-phenoxy)-phenyl]-3-methyl-1,3,5-triazine-2,4,6(1H,3H,5H)-trione and hydrogen peroxide |
| 19 | 1-[3,5-Dichloro-4-(3'-methyl-4'-trifluoromethyl-sulphonyl-phenoxy)-phenyl]-3-methyl-1,3,5-triazine-2,4,6(1H,3H,5H)-trione, melting point 272° C.<br>From: 1-[3,5-Dichloro-4-(3'-methyl-4'-trifluoromethylthio-phenoxy)-phenyl]-3-methyl-1,3,5-triazine-2,4,6-(1H,3H,5H)-trione and hydrogen peroxide. |
| 20 | 1-[4-3,5-Dichloro-(4'-(1,1,2,2-Tetrafluoro-ethylsulfonyl)-phenoxy)-phenyl]3-methyl-1,3,5-triazine-2,4,6(1H,3H,5H)-trione, melting point 251°C<br>From: 1-[3,5-Dichloro-4-(4'-(1,1,2,2-Tetrafluoro ethylthio)-phenoxy)-phenyl]-3-methyl-1,3,5-triazine-2,4,6(1H,3H,5H)-trione and hydrogen peroxide |

The following nonlimitative examples illustrate the production of starting materials which can be used in the above-described process:

EXAMPLE A

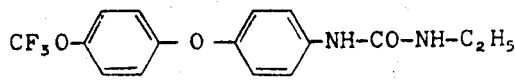

8 g (30 mmols) of 4-amino-4'-trifluoromethoxy-diphenyl-ether of boiling point 129°–130°C (0.3 mm), 40 ml of absolute pyridine and 2.2 g (31 mmols) of ethyl isocyanate were stirred for 10 hours at 100°C. The pyridine was then removed in vacuo and the N-[4-(4'-trifluoromethoxy-phenoxy)-phenyl]-n'-ethyl-urea was recrystallized from ethanol.

Melting point 154°–5°C, yield 60% of theory.

The following ureas can be prepared analogously:

N-[3,5-Dichloro-4-(4'-trifluoromethoxy-phenoxy)-phenyl]-N'-methyl-urea, melting point 184°–5°C.

N-[3,5-Dichloro-4-(4'-trifluoromethylthio-phenoxy)-phenyl]-N'-methyl-urea, melting point 176°C.

N-[4-(4'-Trifluoromethylthio-phenoxy)-phenyl]-N'-methyl-urea, melting point 173°C.

N-[4-(4'-trifluoromethylthio-phenoxy)-phenyl]-N'-ethyl-urea, melting point 143°–4°C.

N-[3,5-Dichloro-4-(4'-trifluoromethylthio-phenoxy)-phenyl]-N'-ethyl-urea, melting point 149°C.

N-[3-Chloro-5-bromo-4-(4'-trifluoromethylthio-phenoxy)-phenyl]-N'-methyl-urea, melting point 173°C.

N-[3,5-Dibromo-4-(4'-trifluoromethylthio-phenoxy)-phenyl]-N'-methyl-urea, melting point 213°C.

N-[3,5-Dichloro-4-(3'-methyl-4'-trifluoromethylthio-phenoxy)-phenyl]-N'-methyl-urea, melting point 158°C.

N-[3,5-Dichloro-4-(4'-1,1,2,2-tetrafluoroethylthio)-phenoxy)-phenyl]-N'-methyl-urea, melting point 115°C.

N-[3,5-Dichloro-4-(4'-trifluoromethylsulphonyl-phenoxy)-phenyl]-N'-methyl-urea, melting point 186°C.

What is claimed:

1. A compound of the formula

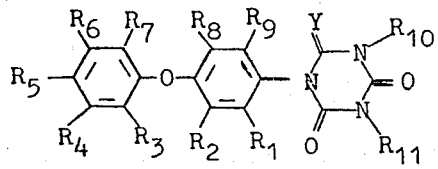

or a pharmaceutically-acceptable, nontoxic salt thereof wherein $R_1$, $R_2$, $R_3$, $R_4$, $R_5$, $R_6$, $R_7$, $R_8$ and $R_9$ are the same or different and each is hydrogen, lower alkyl, halo(lower alkyl), lower alkoxy, halo(lower alkoxy), lower alkylthio, halo(lower alkylthio), halo, nitro, cyano, amino, lower alkanoylamino, lower alkoxycarbonylamino, carboxy, lower alkoxycarbonyl, carbamoyl, lower alkanoyl, halo(lower alkanoyl), lower alkylsulphinyl, lower alkylsulphonyl, halo(lower alkylsulphinyl), halo(lower alkylsulphonyl) or sulphamoyl; provided that at least one of $R_1$, $R_2$, $R_3$, $R_4$, $R_5$, $R_6$, $R_7$, $R_8$ and $R_9$ is halo(lower alkyl), halo(lower alkylthio), halo(lower alkylsulphinyl) or halo(lower alkylsulphonyl);

$R_{10}$ is hydrogen, lower alkyl, cycloalkyl of 4 to 7 carbon atoms, halo(lower alkyl), lower alkoxy, lower alkoxy(lower alkyl), halo(lower alkoxy)(lower alkyl), (lower alkylthio)(lower alkyl), halo(lower alkylthio)(lower alkyl), lower alkenyl, lower alkinyl, lower alkoxycarbonyl, (lower alkylthio)carbonyl, (lower alkylthio)thiocarbonyl, lower alkanoylamino, di(lower alkanoyl)amino, phthalimido, succinimido, di(lower alkyl)amino, benzyl, phenyl or halophenyl;

$R_{11}$ is hydrogen or lower alkyl; and

Y is oxygen or sulphur.

2. A compound according to claim 1 wherein $R_1$, $R_2$, $R_3$, $R_4$, $R_5$, $R_6$, $R_7$, $R_8$ and $R_9$ are the same or different and each is hydrogen, alkyl of 1 to 4 carbon atoms, alkoxy of 1 to 4 carbon atoms, alkylthio of 1 to 4 carbon atoms, trifluoromethyl, chloro, bromo, nitro, cyano, amino, alkanoylamino of 1 to 4 carbon atoms, alkoxycarbonylamino of 1 to 4 carbon atoms in the alkoxy moiety, carboxyl, alkoxycarbonyl of 1 to 4 carbon atoms in the alkoxy moiety, carbamoyl, alkanoyl of 1 to 5 carbon atoms, halo alkanoyl of 1 to 3 halo atoms and 1 to 5 carbon atoms in the acyl moiety, alkylsulphonyl of 1 to 4 carbon atoms, haloalkoxy of 1 to 3 halogen atoms and 1 to 4 carbon atoms in the alkoxy moiety, haloalkylthio of 1 to 7 halogen atoms and 1 to 4 carbon atoms in the alkyl moiety, haloalkylsulphinyl of 1 to 7 halogen atoms and 1 to 4 carbon atoms in the alkyl moiety, or haloalkylsulphonyl of 1 to 7 halogen atoms and 1 to 4 carbon atoms in the alkyl moiety; provided that at least one of $R_1$ through $R_9$ is said haloalkoxy, haloalkylthio, haloalkylsulphinyl, or haloalkylsulphonyl; and $R_{10}$ is hydrogen, straight-chain alkyl of 1 to 12 carbon atoms, branched-chain alkyl of 3 to 5 carbon atoms, chloroalkyl of 1 to 6 carbon atoms, alkoxy of 1 to 6 carbon atoms, alkoxyalkyl of 1 to 6 carbon atoms, haloalkoxyalkyl of 1 to 3 halogen atoms and 1 to 6 carbon atoms, alkenyl of 2 to 4 carbon atoms, alkinyl of 2 to 4 carbon atoms, alkoxycarbonyl of 1 to 4 carbon atoms, alkylthiocarbonyl of 1 to 4 carbon atoms, dialkylamino wherein each alkyl moiety is the same alkyl moiety of 1 to 4 carbon atoms, acylamino of 1 to 5 carbon atoms, dialkanoylamino of 1 to 5 carbon atoms in each alkanoyl moiety, phthalimido, succinimido, phenyl or halophenyl.

3. A compound according to claim 1 wherein $R_1$, $R_2$, $R_3$, $R_4$, $R_5$, $R_6$, $R_7$, $R_8$ and $R_9$ are the same or dif- and each is hydrogen, alkyl of 1 to 4 carbon atoms, alkoxy of 1 to 4 carbon atoms, alkylthio of 1 to 4 carbon atoms, trifluoromethyl, chloro, bromo, nitro, cyano, amino alkanoylamino of 1 to 4 carbon atoms, alkoxycarbonylamino of 1 to 4 carbon atoms in the alkoxy moiety, carboxyl, alkoxycarbonyl of 1 to 4 carbon atoms in the alkoxy moiety, carbamoyl, alkanoyl of 1 to 4 carbon atoms, trifluoroacetyl, alkylsulphonyl of 1 to 4 carbon atoms, trifluoromethoxy, trifluoromethylthio, trifluoromethylsulphinyl, trifluoromethylsulphonyl; provided that at least one of $R_1$ through $R_9$ is trifluoromethoxy, trifluoromethylthio, trifluoromethylsulphinyl, or trifluoromethylsulphonyl; and $R_{10}$ is hydrogen, straight-chain alkyl of 1 to 12 carbon atoms, branched-chain alkyl of 3 to 5 carbon atoms, chloroalkyl of 1 to 6 carbon atoms, alkoxy of 1 to 6 carbon atoms, alkoxyalkyl of 1 to 6 carbon atoms, trifluoromethoxymethyl, alkenyl of 2 to 4 carbon atoms, alkinyl of 2 to 4 carbon atoms, alkoxycarbonyl of 1 to 4 carbon atoms, alkylthiocarbonyl of 1 to 4 carbon atoms, dialkylamino wherein each alkyl moiety is the same alkyl moiety of 1 to 4 carbon atoms, alkanoylamino of 1 to 5 carbon atoms, phthalimido, succinimido, phenyl or halophenyl.

4. A compound according to claim 1 wherein
$R_1$, $R_2$, $R_3$, $R_4$, $R_5$, $R_6$, $R_7$, $R_8$ and $R_9$ are the same or different and each is hydrogen, alkyl of 1 or 2 carbon atoms, trifluoroalkyl of 1 or 2 carbon atoms, alkoxy of 1 or 2 carbon atoms, trifluoroalkoxy of 1 or 2 carbon, alkylthio of 1 or 2 carbon atoms, trifluoroalkylthio of 1 to 2 carbon atoms, tetrafluoroalkylthio of 2 carbon atoms, chloro, bromo, nitro, cyano, alkylsulphonyl of 1 or 2 carbon atoms, trifluoroalkylsulphinyl of 1 or 2 carbon atoms, trifluoroalkylsulphonyl of 1 or 2 carbon atoms or tetrafluoroalkyl sulfonyl of 2 carbon atoms; provided that at least 1 of $R_1$ through $R_9$ is said trifluoroalkyl, trifluoroalkylthio, trifluoroalkylsulphinyl, or trifluoroalkylsulphonyl;
$R_{10}$ is hydrogen, alkyl of 1 or 2 carbon atoms, alkenyl of 2 or 3 carbon atoms, alkoxycarbonyl of 1 or 2 carbon atoms in the alkyl moiety, dialkylamino wherein the alkyl moieties are the same and each are alkyl of 1 or 2 carbon atoms, phthalimido or alkoxy of 1 or 2 carbon atoms;
$R_{11}$ is hydrogen or alkyl of 1 to 3 carbon atoms; and
Y is oxygen.

5. A compound according to claim 1 wherein
$R_1$, $R_2$, $R_3$, $R_4$, $R_5$, $R_6$, $R_7$, $R_8$ and $R_9$ are the same or different and each is hydrogen, methyl, methoxy, trifluoromethoxy, trifluoromethylthio, chloro, bromo, nitro, cyano, methylsulphonyl, trifluoromethylsulphinyl or trifluoromethylsulphonyl; provided that at least one of $R_1$ to $R_9$ is trifluoromethylthio, trifluoromethylsulphinyl, or trifluoromethylsulphonyl;
$R_{10}$ is hydrogen, methyl, methoxy, methoxycarbonyl, allyl, dimethylamino or phthalimido; and
Y is oxygen.

6. A compound according to claim 1 wherein
$R_1$, $R_2$, $R_8$ and $R_9$ are each selected from the group consisting of hydrogen, methyl, chloro, bromo, and trifluoromethylthio;
$R_3$, $R_4$, $R_5$, $R_6$ and $R_7$ are each selected from the group consisting of hydrogen, methyl, methoxy, trifluoromethoxy, trifluoromethylthio, chloro, bromo, nitro, cyano, methylsulphonyl, trifluoromethylsulphinyl, and trifluoromethylsulphonyl; provided that at least one of $R_1$ to $R_9$ is trifluoromethylthio, trifluoromethylsulphinyl, or trifluoromethylsulphonyl;
$R_{10}$ is hydrogen, methyl, methoxy, methoxycarbonyl, allyl, dimethylamino, or phthalimido; and
Y is oxygen.

7. A compound according to claim 1 wherein
$R_1$, $R_2$, $R_3$, $R_4$, $R_5$, $R_6$, $R_7$, $R_8$ and $R_9$ are the same or different and each is hydrogen, alkyl of 1 or 2 carbon atoms, trifluoroalkoxy of 1 or 2 carbon atoms, trifluoroalkylthio of 1 or 2 carbon atoms in the alkyl moiety, tetrafluroalkylthio of 2 carbon atoms in the alkyl moiety, chloro, bromo, trifluoroalkylsulphonyl of 1 or 2 carbon atoms; or tetrafluoroalkylsulfonyl of 2 carbon atoms; provided that at least 1 of $R_1$ through $R_9$ is trifluoroalkylthio of 1 or 2 carbon atoms, tetrafluoroalkylthio of 2 carbon atoms, trifluoroalkylsulphonyl of 1 or 2 carbon atoms or tetrafluoroalkylsulfonyl of 2 carbon atoms;
$R_{10}$ is hydrogen or alkyl of 1 or 2 carbon atoms;
$R_{11}$ is alkyl of 1 or 2 carbon atoms; and
Y is oxygen.

8. A compound according to claim 1 wherein
$R_1$, $R_2$, $R_3$, $R_4$, $R_5$, $R_6$, $R_7$, $R_8$ and $R_9$ are the same or different and each is hydrogen, methyl, trifluoromethoxy, trifluoromethylthio, tetrafluoroethylthio, chloro, bromo, trifluoromethylsulphonyl, or tetrafluoroethylsulfonyl; provided that at least one of $R_1$ through $R_9$ is trifluoromethylthio, tetrafluoroethylthio, trifluoromethylsulphonyl, or tetrafluoromethylsulfonyl;
$R_{10}$ is hydrogen or methyl;
$R_{11}$ is methyl or ethyl; and
Y is oxygen.

9. A compound according to claim 1 wherein
$R_1$, $R_3$, $R_4$, $R_7$ and $R_9$ are each hydrogen;
$R_2$ is hydrogen, methyl, chloro or bromo;
$R_5$ is trifluoromethoxy, trifluoromethylthio, 1,1,2,2-tetrafluoroethylthio, trifluoromethylsulphonyl, or 1,1,2,2-tetrafluoroethylsulfonyl
$R_6$ is hydrogen or methyl;
$R_8$ is hydrogen, methyl, chloro or bromo;
$R_{10}$ is hydrogen or methyl;
$R_{11}$ is methyl or ethyl; and
Y is oxygen.

10. The compound according to claim 1 which is 1-[4-(4'-trifluoromethoxy-phenoxy)-phenyl]-3-ethyl-1,3,5-triazine-2,4,6(1H, 3H, 5H)-trione.

11. The compound according to claim 1 which is 1-[3,5-dichloro-4-(4'-trifluoromethoxy-phenoxy)-phenyl]-3-methyl-1,3,5-triazine-2,4,6(1H, 3H, 5H)-trione.

12. The compound according to claim 1 which is 1-[3,5-dichloro-4-(4'-trifluoromethylthiophenoxy)-phenyl]-3-methyl-1,3,5-triazine-2,4,6(1H, 3H, 5H)-trione.

13. The compound according to claim 1 which is 1-[4-(4'-trifluoromethylthio-phenoxy)-phenyl]-3-ethyl-1,3,5-triazine-2,4,6(1H, 3H, 5H)-trione.

14. The compound according to claim 1 which is 1-[4-(4'-trifluoromethylthio-phenoxy)-phenyl]-3-methyl-1,3,5-triazine-2,4,6(1H, 3H, 5H)-trione.

15. The compound according to claim 1 which is 1-[3,5-dichloro-4-(4'-trifluoromethylthio-phenoxy)-phenyl]-3-ethyl-1,3,5-triazine-2,4,6(1H, 3H, 5H)-trione.

16. The compound according to claim 1 which is 1-[3-chloro-5-bromo-4-(4'-trifluoromethylthio-phenoxy)-phenyl]-3-methyl-1,3,5-triazine-2,4,6(1H, 3H, 5H)-trione.

17. The compound according to claim 1 which is 1-[3,5-dibromo-4-(4'-trifluoromethylthio-phenoxy)-phenyl]-3-methyl-1,3,5-triazine-2,4,6(1H, 3H, 5H)-trione.

18. The compound according to claim 1 which is 1-[3,5-dichloro-4-(3'-methyl-4'-trifluoromethylthio-phenoxy)-phenyl]-3-methyl-1,3,5-triazine-2,4,6(1H, 3H, 5H)-trione.

19. The compound according to claim 1 which is

1-[3,5-Dichloro-4-(4'-1,1,2,2-tetrafluoroethylthio)-phenoxy-phenyl]-3-methyl-1,3,5-triazine-2,4,6-(1H, 3H, 5H)-trione.

20. The compound according to claim 1 which is 1-[3,5-dichloro-4-(4'-trifluoromethylthio-phenoxy)-phenyl]-3,5-dimethyl-1,3,5-triazine-2,4,6(1H, 3H, 5H)-trione.

21. The compound according to claim 1 which is 1-[4-(4'-trifluoromethylsulphonyl-phenoxy)-phenyl]-3-ethyl-1,3,5-triazine-2,4,6(1H, 3H, 5H)-trione.

22. The compound according to claim 1 which is 1-[4-(4'-trifluoromethylsulphonyl-phenoxy)-phenyl]-3-methyl-1,3,5-triazine-2,4,6(1H, 3H, 5H)-trione.

23. The compound according to claim 1 which is 1-[3,5-dichloro-4-(4'-trifluoromethylsulphonyl-phenoxy)-phenyl]-3-methyl-1,3,5-triazine-2,4,6(1H, 3H, 5H)-trione.

24. The compound according to claim 1 which is 1-[3,5-dichloro-4-(4'-trifluoromethylsulphonyl-phenoxy)-phenyl]-3-ethyl-1,3,5-triazine-2,4,6(1H, 3H, 5H)-trione.

25. The compound according to claim 1 which is 1-[3,5-dichloro-4-(4'-trifluoromethylsulphonyl-phenoxy)-phenyl]-3,5-dimethyl-1,3,5-triazine-2,4,6(1H, 3H, 5H)-trione.

26. The compound according to claim 1 which is 1-[3-chloro-5-bromo-4-(4'-trifluoromethylsulphonyl-phenoxy)-phenyl]-3-methyl-1,3,5-triazine-2,4,6(1H, 3H, 5H)-trione.

27. The compound according to claim 1 which is 1-[3,5-dibromo-4-(4'-trifluoromethylsulphonyl-phenoxy)-phenyl]-3-methyl-1,3,5-triazine-2,4,6(1H, 3H, 5H)-trione.

28. The compound according to claim 1 which is 1-[3,5-dichloro-4-(3'-methyl-4'-trifluoromethyl-sulphonyl-phenoxy)-phenyl]-3-methyl-1,3,5-triazine-2,4,6(1H, 3H, 5H)-trione.

29. The compound according to claim 1 which is 1-[3,5-Dichloro-4-(4'-(1,1,2,2-tetrafluoroethylsulphonyl)-phenoxy)-phenyl]-3-methyl-1,3,5-triazine-2,4,6(1H, 3H, 5H)-trione.

* * * * *